US00PP12590P2

(12) United States Plant Patent
van Rijn

(10) Patent No.: US PP12,590 P2
(45) Date of Patent: Apr. 30, 2002

(54) ANTHURIUM PLANT NAMED 'WHITE QUEEN'

(75) Inventor: Leonardus van Rijn, Schipluiden (NL)

(73) Assignee: Rijnplant, Schipluiden (NL)

( * ) Notice: Subject to any disclaimer, the term of this patent is extended or adjusted under 35 U.S.C. 154(b) by 0 days.

(21) Appl. No.: 09/563,939

(22) Filed: May 4, 2000

(51) Int. Cl.[7] ..... A01H 5/00

(52) U.S. Cl. ..... Plt./366

(58) Field of Search ..... Plt./366

(56) References Cited

PUBLICATIONS

UPOV–ROM GTITM Computer database, GTI JOUVE retrieval software, citations for 'White Queen'.*

* cited by examiner

*Primary Examiner*—Bruce R. Campell
*Assistant Examiner*—Wendy C. Baker
(74) *Attorney, Agent, or Firm*—C. A. Whealy

(57) ABSTRACT

A distinct cultivar of Anthurium plant named 'White Queen', characterized by its upright and somewhat outwardly spreading plant habit; freely clumping growth habit; durable glossy dark green leaves; strong root system; white-colored spathes that are positioned upright and beyond the foliage on strong and erect scapes; and good post-production longevity.

2 Drawing Sheets

BACKGROUND OF THE INVENTION

The present invention relates to a new and distinct cultivar of Anthurium plant, botanically known as *Anthurium andreanum,* and hereinafter referred to by the cultivar name White Queen.

The new Anthurium is a product of a planned breeding program conducted by the Inventor in Schipluiden, The Netherlands. The objective of the program is to create and develop new Anthurium cultivars that have a freely clumping growth habit, durable leaves and spathes, strong roots, attractive spathe color, and good post-production longevity.

The new Anthurium originated from a cross by the Inventor in July, 1995 of the Inventor's proprietary *Anthurium andreanum* selection code number 92-3 as the female, or seed, parent with the Inventor's proprietary *Anthurium andreanum* selection code number 0023 as the male, or pollen, parent. The cultivar White Queen was discovered and selected by the Inventor as a plant within the progeny of the stated cross in a controlled environment in Schipluiden, The Netherlands in April, 1997.

Asexual propagation of the new cultivar of tissue culture of meristem tips in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar White Queen. These characteristics in combination distinguish 'White Queen' as a new and distinct cultivar:

1. Upright and somewhat outwardly spreading plant habit.
2. Freely clumping growth habit.

3. Durable dark green glossy leaves.
4. Strong root system.
5. White-colored spathes that are positioned upright and beyond the foliage on strong and erect scapes.
6. Good post-production longevity.

The new Anthurium can be compared to the female parent, the Inventor's proprietary selection code number 92-3. In side-by-side comparisons conducted in Schipluiden, The Netherlands, plants of the new Anthurium differ from plants of selection code number 92-3 in the following characteristics:

1. Plants of the new Anthurium are more outwardly spreading and more freely clumping than plants of the selection code number 92-3.
2. Plants of the new Anthuirium have smaller leaves than plants of the selection code number 92-3.
3. Spathe color of the new Anthurium is white whereas spathe color of the selection code number 92-3 is pink.
4. Spathes of the new Anthurium are closer to the foliage than spathes of the selection code number 92-3.

The new Anthurium can be compared to the male parent, the Inventor's proprietary selection code number 0023. In side-by-side comparisons conducted in Schipluiden, The Netherlands, plants of the new Anthurium differ from plants of selection code number 0023 in the following characteristics:

1. Plants of the new Anthurium are larger and not as compact as plants of the selection code number 0023.
2. Plants of the new Anthurium are faster growing than plants of the selection code number 0023.
3. Plants of the new Anthurium have much larger spathes with longer spadices than plants of the selection code number 0023.

The new Anthurium can be compared to the Anthurium cultivar Cleopatra, U.S. Plant Pat. No. 11,456. In side-by-side comparisons conducted in Schipluiden, The Netherlands, plants of the new Anthurium differ from plants of the cultivar Cleopatra in the following characteristics:

1. Plants of the new Anthurium have smaller leaves than plants of the cultivar Cleopatra.

2. Plants of the new Anthurium have flatter spathes than plants of the cultivar Cleopatra.

3. Spadices of the new Anthurium are weakly recurved whereas spadices of the cultivar Cleopatra are straight.

4. Spadices of the new Anthurium have yellow-colored apices whereas spadices of the cultivar Cleopatra have red-colored apices.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which more accurately describe the actual colors of the new Anthurium.

The photograph on the first sheet comprises a top perspective view of a typical potted plant of the cultivar White Queen.

The photograph on the second sheet comprises a close-up view of typical leaves and inflorescences of the cultivar White Queen.

DETAILED BOTANICAL DESCRIPTION

In the following description, color references are made to The Royal Horticultural Society Colour Chart except where general terms of ordinary dictionary significance are used. The following observations and measurements describe 40-week old plants grown in 17-cm containers in Schipluiden, The Netherlands, in a glass greenhouse with an average day temperature of 25° C. and an average night temperature of 19° C.

Botanical classification: *Anthurium andreanum* cultivar White Queen.

Parentage:

*Female parent.*—Inventor's proprietary *Anthurium andreanum* selection code number 92-3, not patented.

*Male parent.*—Inventor's proprietary *Anthurium andreanum* selection code number 0023, not patented.

Propagation:

*Method.*—Typically by tissue culture of meristem tips.

*Time to initiate roots.*—About 70 or 84 days at 24° C. or 21° C., respectively.

*Rooting description.*—Numerous and very strong fleshy roots.

Plant description:

*Plant shape.*—Upright and somewhat outwardly spreading, inverted triangle, symmetrical.

*Growth habit.*—Freely clumping, bushy and dense. Appropriate for 17 to 35-cm containers.

*Plant height.*—About 55 cm.

*Plant diameter.*—About 87 cm.

*Plant vigor.*—High.

*Growth rate.*—Moderate to rapid.

*Crop time.*—About 10 months are usually required from planting of young plants to finished plants in a 17-cm container.

*Foliage description.*—Quantity per plant: About 20 to 30. Length: About 13 to 21 cm. Width: About 10 to 18.5 cm. Shape: Narrowly cordate. Apex: Apiculate. Base: Auriculate to cordate; lobes occasionally overlapping. Margin: Entire. Texture: Smooth, glabrous, leathery; glossy. Color: Young leaves, upper surface: 146A. Young leaves, lower surface: 146B. Mature leaves, upper surface: 147A. Mature leaves, lower surface: 146C. Petiole: Length: About 25 to 39 cm. Color: 144A. Geniculum length: About 2 to 3 cm. Geniculum diameter: About 5 to 7 mm. Geniculum color: 146B. Geniculum angle: Erect to about 30° C.

Inflorescence description:

*Inflorescence arrangement.*—Spathes with spadices held beyond the foliage. Flowering structures arise from leaf axils. Freely flowering; continuous flowering year-round; typically about ten inflorescences per plant.

*Inflorescence longevity.*—Inflorescences last about six weeks under winter conditions and about three months under summer conditions; persistent.

*Flowers.*—Quantity per spadix: Numerous, about 100 to 150. Shape: Rounded. Diameter: About 1 mm, maximum.

*Spathe.*—Length: About 5.8 to 9 cm. Width: About 9 to 12.5 cm. Shape: Deltoid, cordate. Apex: Apiculate. Base: Auriculate to cordate; lobes not overlapping. Margin: Entire. Texture: Leathery, glabrous, slight blistering, glossy. Color: When opening: 155D. Opened, front surface: 155D. Opened, rear surface: 155D. After senescence: 155D.

*Spadix.*—Length: About 6 to 8 cm. Diameter: About 1 cm. Shape: Columnar. Cross section: Ronded. Longitudinal axis: Very weakly recurved. Color: Apex: 25B. Mid-section: 38C. Base: 36C. After senescence: 151B.

*Scape.*—Length: About 23 to 46 cm. Aspect: Strong and erect. Color: 144A.

*Reproductive organs.*—Androecium: Pollen color: Close to 159C. Gynoecium: Stigma shape: Ovoid.

Disease resistance: Under commercial conditions, plants of the new Anthurium have exhibited good tolerance to root diseases common to Anthurium.

Seed development: Seed development on plants of the new Anthurium has not been observed.

It is claimed:

1. A new and distinct cultivar of Anthurium plant named 'White Queen', as illustrated and described.

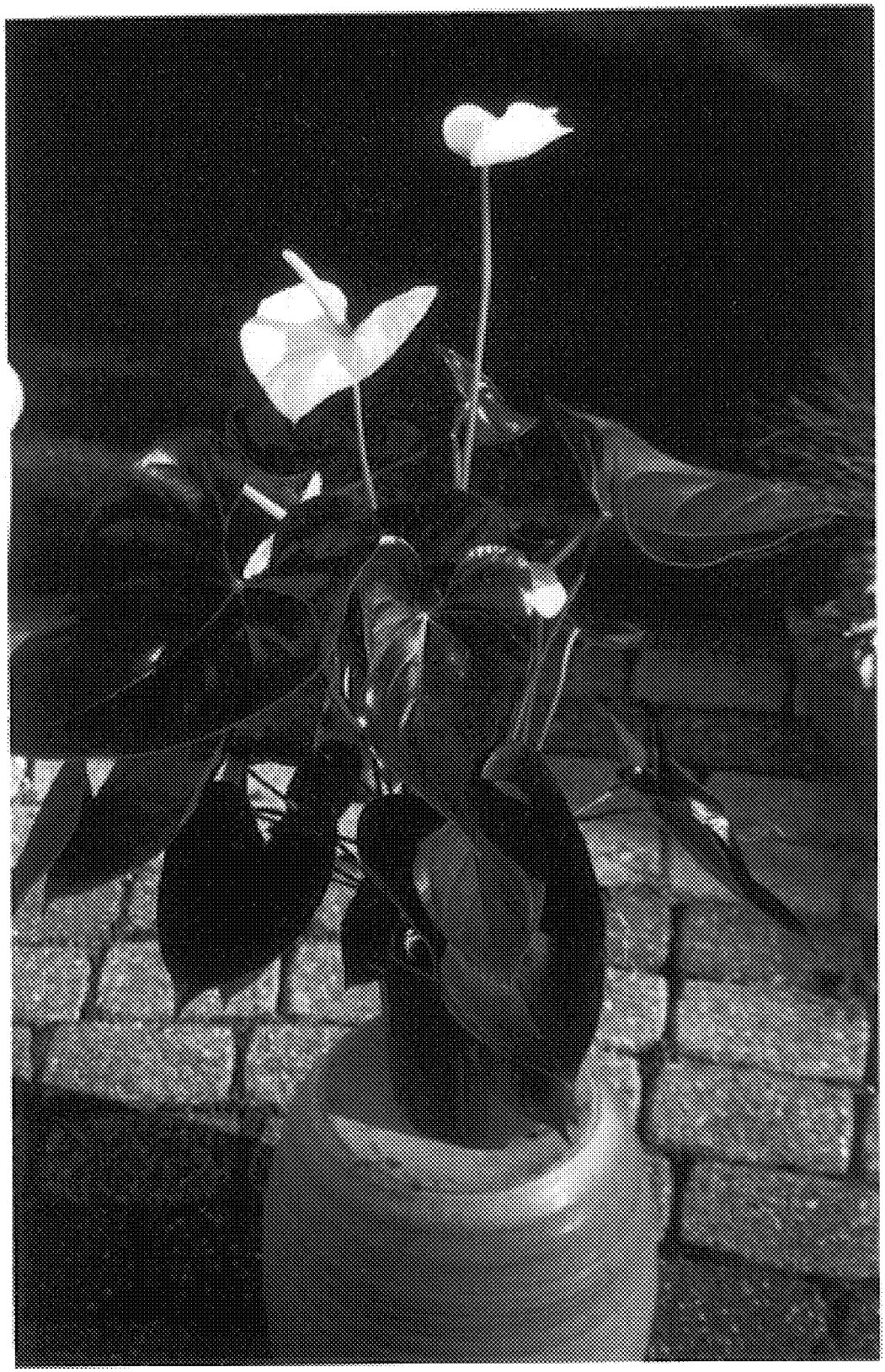

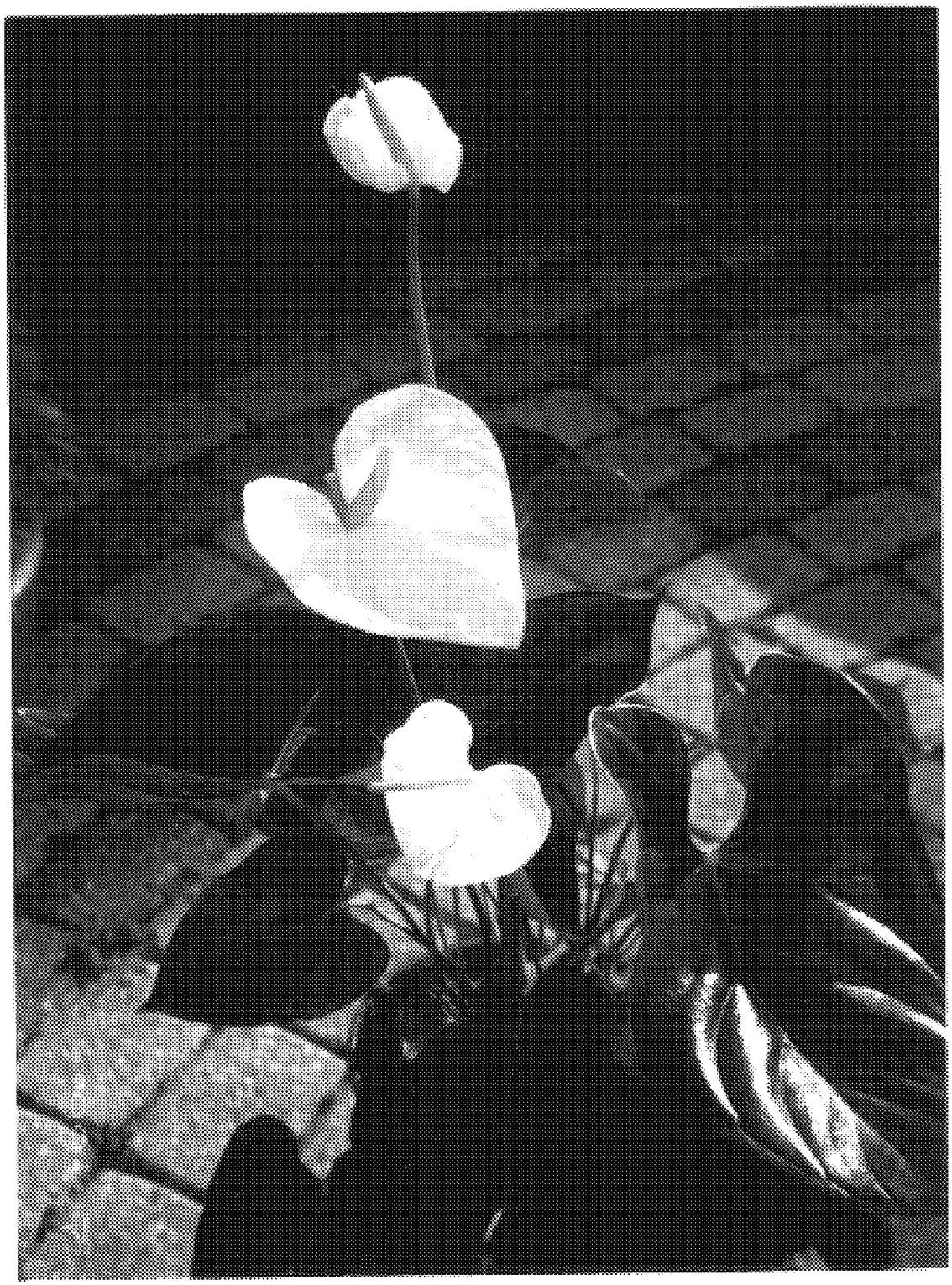

* * * * *